United States Patent [19]

Ota et al.

[11] Patent Number: 5,312,707
[45] Date of Patent: May 17, 1994

[54] ELECTROPHOTOGRAPHIC PHOTOCONDUCTOR AND DIAMINE COMPOUNDS FOR USE IN THE SAME

[75] Inventors: Masafumi Ota; Masaomi Sasaki, both of Susono; Tamotsu Aruga, Mishima; Tomoyuki Shimada, Shizuoka; Mitsutoshi Anzai, Kawagoe; Masaki Okubo, Ushiku, all of Japan

[73] Assignees: Ricoh Company, Ltd.; Hodogaya Chemical Co., Ltd., both of Tokyo, Japan

[21] Appl. No.: 953,841

[22] Filed: Sep. 30, 1992

[30] Foreign Application Priority Data

| | | |
|---|---|---|
| Sep. 30, 1991 [JP] | Japan | 3-278648 |
| Oct. 30, 1991 [JP] | Japan | 3-311988 |
| Dec. 9, 1991 [JP] | Japan | 3-350313 |
| Jul. 20, 1992 [JP] | Japan | 4-214613 |
| Aug. 10, 1992 [JP] | Japan | 4-234319 |

[51] Int. Cl.$^5$ .................. G03G 5/047; G03G 5/09
[52] U.S. Cl. .................................. 430/59; 430/83
[58] Field of Search .................................. 430/59, 83

[56] References Cited

U.S. PATENT DOCUMENTS

| | | | |
|---|---|---|---|
| 4,233,384 | 11/1980 | Turner et al. | 430/59 |
| 5,079,118 | 1/1992 | Kikuchi et al. | 430/59 |

FOREIGN PATENT DOCUMENTS

253753 10/1989 Japan .................. 430/59

*Primary Examiner*—Roland Martin
*Attorney, Agent, or Firm*—Oblon, Spivak, McClelland, Maier & Neustadt

[57] ABSTRACT

An electrophotographic photoconductor is composed of an electroconductive substrate and a photoconductive layer formed thereon including a diamine compound of formula (I):

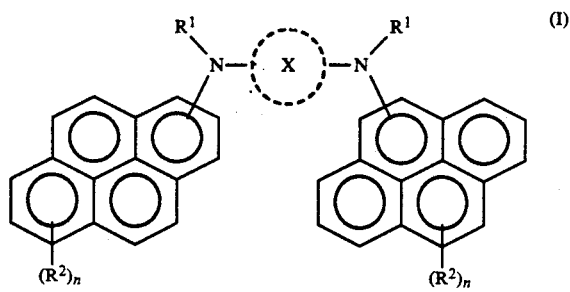

wherein $R^1$ represents an alkyl group having 1 to 4 carbon atoms, or an aryl group; $R^2$ represents hydrogen, an alkyl group having 1 to 4 carbon atoms, or an alkoxyl group having 1 to 4 carbon atoms; n is an integer of 1 to 3; and

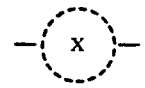

represents an arylene group or a bivalent group of a heterocyclic compound. A diamine compound for use in the electrophotographic photoconductor is also disclosed.

23 Claims, 2 Drawing Sheets

ELECTROPHOTOGRAPHIC PHOTOCONDUCTOR AND DIAMINE COMPOUNDS FOR USE IN THE SAME

BACKGROUND OF THE INVENTION

1. Field of the Invention

The present invention relates to an electrophotographic photoconductor comprising an electroconductive substrate and a photoconductive layer formed thereon comprising at least one diamine compound, and the diamine compounds for use in the above photoconductor.

2. Discussion of Background

Conventionally, inorganic materials such as selenium, cadmium sulfide and zinc oxide are used as photoconductive materials for electrophotographic photoconductors in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by toner particles comprising a coloring agent such as a dye and a pigment, and a binder agent such as a polymeric material, to a visible image.

Fundamental characteristics required for the photoconductor for use in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be obtained by coating a dispersion of cadmium sulfide particles and zinc oxide particles respectively in a binder resin on a substrate. However, they are poor in mechanical properties, such as surface smoothness, hardness, tensile strength and wear resistance. Therefore, they cannot be used in the repeated operation.

To solve the problems of the inorganic materials, various electrophotographic photoconductors employing organic materials have been proposed recently and some are put to practical use. For example, there are known a photoconductor comprising poly-N-vinylcarbazole and 2,4,7-trinitrofluorene-9-one, as disclosed in U.S. Pat. No. 3,484,237; a photoconductor prepared by sensitizing poly-N-vinylcarbazole with a pigment of pyrylium salt, as described in Japanese Patent Publication 48-25658; a photoconductor comprising as the main component an organic pigment, as described in Japanese Laid-Open Patent Application 47-37543; a photoconductor comprising as the main component an eutectic crystal complex of a dye and a resin, as described in Japanese Laid-Open Patent Application 47-10735; a photoconductor prepared by sensitizing a triphenylamine compound with a sensitizer pigment, as described in U.S. Pat. No. 3,180,730; a photoconductor comprising an amine derivative as a charge transporting material, as described in Japanese Laid-Open Patent Application 57-195254; a photoconductor comprising poly-N-vinylcarbazole and an amine derivative as charge transporting materials, as described in Japanese Laid-Open Patent Application 58-1155; and a photoconductor comprising a polyfunctional tertiary amine compound, in particular benzidine compound, as a photoconductive material, as described in U.S. Pat. No. 3,265,496, Japanese Patent Publication 39-11546 and Japanese Laid-Open Patent Application 53-27033.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements in electrophotography.

SUMMARY OF THE INVENTION

It is therefore a first object of the present invention to provide an electrophotographic photoconductor free from the conventional shortcomings, which can completely satisfy all the requirements in the electrophotographic process, including high durability, and can be easily manufactured at a relatively low cost.

A second object of the present invention is to provide novel diamine compounds serving a photoconductive materials for use in the above-mentioned electrophotographic photoconductor.

The first object of the present invention can be achieved by an electrophotographic photoconductor comprising an electroconductive substrate and a photoconductive layer formed thereon comprising at least one diamine compound of formula (I):

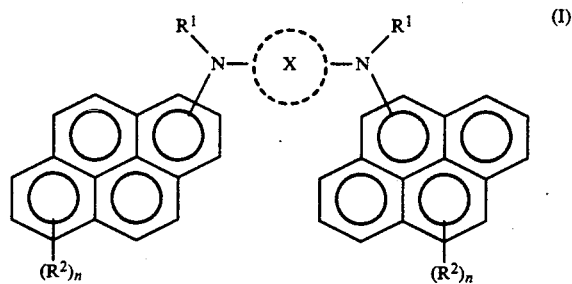

wherein $R^1$ represents an alkyl group having 1 to 4 carbon atoms, or an aryl group; $R^2$ represents hydrogen, an alkyl group having 1 to 4 carbon atoms, or an alkoxyl group having 1 to 4 carbon atoms; n is an integer of 1 to 3; and

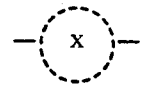

represents an arylene group or a bivalent group of a heterocyclic compound.

The second object of the present invention can be achieved by the above-mentioned diamine compounds of formula (I).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
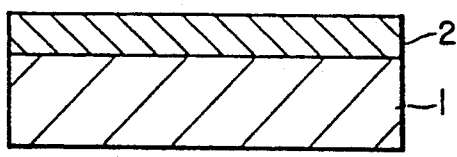
FIG. 1 is a schematic cross-sectional view of a first example of an electrophotographic photoconductor according to the present invention.

An electrophotographic photoconductor of the present invention comprises an electroconductive substrate and a photoconductive layer formed thereon comprising at least one diamine compound of formula (I):

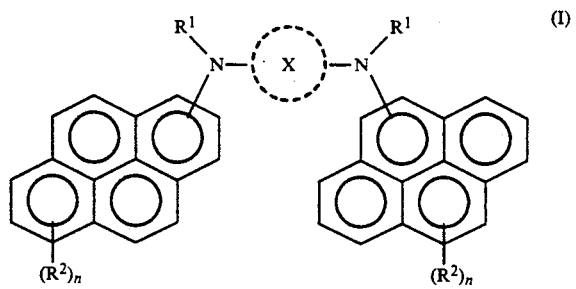

wherein $R^1$ represents an alkyl group having 1 to 4 carbon atoms, or an aryl group; $R^2$ represents hydrogen, an alkyl group having 1 to 4 carbon atoms, or an alkoxyl group having 1 to 4 carbon atoms; n is an integer of 1 to 3; and

represents an arylene group or a bivalent group of a heterocyclic compound.

The aryl group represented by $R^1$ in formula (I) is a non-condensed hydrocarbon group or condensed polycyclic hydrocarbon group.

Specific examples of the non-condensed hydrocarbon group are phenyl group, biphenyl group, and terphenyl group.

It is preferable that the condensed polycyclic hydrocarbon group have 18 carbon atoms or less in a ring of the group. Specific examples of such a condensed polycyclic hydrocarbon group are pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

Specific examples of the arylene group represented by

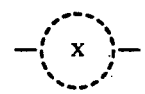

in formula (I) are bivalent groups of monocyclic hydrocarbon compounds such as benzene, diphenyl ether, polyethylene glycol diphenyl ether, diphenyl thioether, and diphenyl sulfone; bivalent groups of non-condensed polycyclic hydrocarbon compounds such as biphenyl, polyphenyl, diphenylalkane, diphenylpolyene, diphenylpoly-yne, triphenylmethane, distyrylbenzene, 1,1-diphenylcycloalkane, polyphenylalkane, and polyphenylalkene; bivalent groups of condensed polycyclic hydrocarbon compounds corresponding to those represented by $R^1$, such as pentalenediyl, indenediyl, naphthalenediyl, azulenediyl, heptalenediyl, biphenylenediyl, as-indacenediyl, fluorenediyl, s-indacenediyl, acenaphthylenediyl, pleiadenediyl, acenaphthenediyl, phenalenediyl, phenanthrenediyl, anthracenediyl, fluoranthenediyl, acephenanthrylenediyl, aceanthrylenediyl, triphenylenediyl, pyrenediyl, chrysenediyl, and naphthacenediyl; and bivalent groups of hydrocarbon ring assemblies such as 9,9-diphenylfluorene.

also represents bivalent groups of heterocyclic compounds such as carbazole, dibenzofuran, dibenzothiophene, oxadiazole, and thiadiazole.

The aryl group represented by $R^1$ and the arylene group or the bivalent heterocyclic group represented

may have a substituent. Examples of the substituent are as follows: (1) A halogen atom, a cyano group and a nitro group. (2) A straight chain or branched chain alkyl group having 1 to 12 carbon atoms, more preferably an alkyl group having 1 to 8 carbon atoms, and further preferably an alkyl group having 1 to 4 carbon atoms, which may have a substituent.

Specific examples of the above alkyl group include methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

Specific examples of the substituent of the above alkyl group are hydroxyl group, cyano group, alkoxyl group having 1 to 4 carbon atoms, phenyl group, a halogen atom, phenyl group substituted with alkyl group having 1 to 4 carbon atoms, and phenyl group substituted with alkoxyl group having 1 to 4 carbon atoms.

(3) An alkoxyl group represented by $-OR^5$, in which $R^5$ represents the same alkyl group which may have a substituent as defined in (2).

Specific examples of the above alkoxyl group include methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group, and trifluoromethoxy group.

(4) An aryloxy group, in which an aryl group represents, for example, a phenyl group and a naphthyl group. The above aryloxy group may have a substituent such as an alkoxyl group having 1 to 4 carbon atoms, an alkyl group having 1 to 4 carbon atoms or a halogen atom.

Specific examples of the above aryloxy group include phenoxy group, 1-naphthyloxy group, 2-naphthyloxy group, 4-methylphenoxy group, 4-methoxyphenoxy group, 4-chlorophenoxy group and 6-methyl-2-naphthyloxy group.

(5) A substituted mercapto group represented by $-SR^6$, in which $R^6$ represents an alkyl group having 1 to 12 carbon atoms or an aryl group. It is preferable that the alkyl group represented by $R^6$ have 1 to 8 carbon atoms, more preferably 1 to 4 carbon atoms. The aryl group represented by $R^6$ is the same as that represented by $R^1$ in formula (I).

Specific examples of the above substituted mercapto group include methylthio group, ethylthio group, phenylthio group and p-methylphenylthio group.

(6)

in which $R^7$ and $R^8$ independently represent hydrogen, the same alkyl group which may have a substituent as defined in (2) or an aryl group which may have a substituent. As the aryl group, phenyl group, biphenyl group or naphthyl group can be employed, which may have a substituent such as an alkoxyl group having 1 to 4 carbon atoms, an alkyl group having 1 to 4 carbon atoms or a halogen atom. $R^7$ and $R^8$ may form a ring in combination, or in combination with carbon atoms on the aryl group.

Specific examples of the above

include an amino group, diethylamino group, N-methyl-N-phenylamino group, N,N-diphenylamino group, N,N-di(p-tolyl)amino group, dibenzylamino group, piperidino group, morpholino group and julolidyl group.

(7) An alkylenedioxy group such as methylenedioxy group, or an alkylenedithio group such as methylenedithio group.

Specific examples of the diamine compounds of formula (I) are shown in the following Table 1:

TABLE 1

| Compound No. | —(X)— | $R^1$ | $R^2$ | Position of Substituent on Pyrene Ring |
|---|---|---|---|---|
| 1 | phenyl | $C_2H_5$ | H | 1- |
| 2 | phenyl | phenyl | H | 1- |
| 3 | phenyl | 3-methylphenyl | H | 1- |
| 4 | phenyl | 2-methylphenyl | H | 1- |

TABLE 1-continued
| Compound No. | —X— | R¹ | R² | Position of Substituent on Pyrene Ring |
|---|---|---|---|---|
| 5 |  | 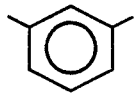 CH₃ | H | 1- |
| 6 | 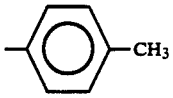 | 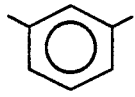 OCH₃ | H | 1- |
| 7 | 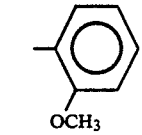 | 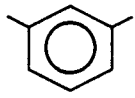 OCH₃ | H | 1- |
| 8 | 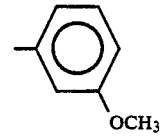 | 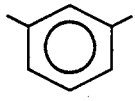 OCH₃ | H | 1- |
| 9 | 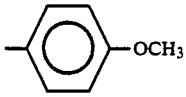 | 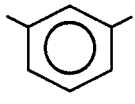 CH₃, CH₃ | H | 1- |
| 10 | 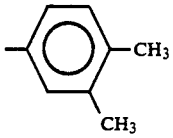 | 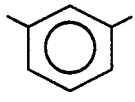 OCH₃, OCH₃ | H | 1- |
| 11 | 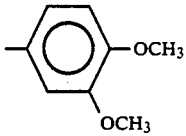 | 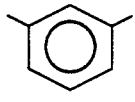 | H | 1- |
| 12 | 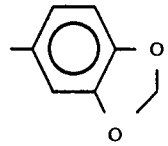 | 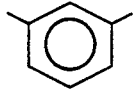 CH₃ | H | 2- |
| 13 | 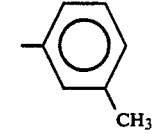 | 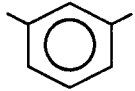 CH₃ | H | 4- |
| 14 | 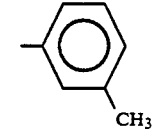 | 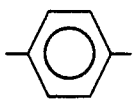 CH₃ | H | 1- |

TABLE 1-continued
| Compound No. | —X— | $R^1$ | $R^2$ | Position of Substituent on Pyrene Ring |
|---|---|---|---|---|
| 15 |  |  | H | 1- |
| 16 |  | 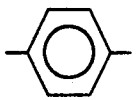 | H | 1- |
| 17 | 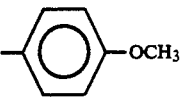 |  | H | 1- |
| 18 | 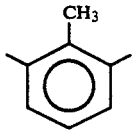 | 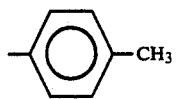 | H | 1- |
| 19 |  | 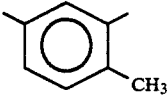 | H | 1- |
| 20 | 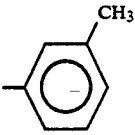 |  | H | 1- |
| 21 | 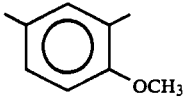 | 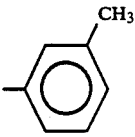 | H | 1- |
| 22 |  | 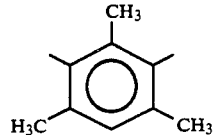 | H | 1- |
| 23 | 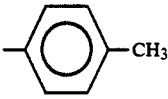 |  | H | 1- |
| 24 | 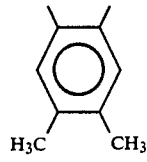 | 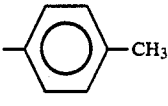 | H | 1- |

TABLE 1-continued

| Compound No. | —⬡(X)⬡— | R¹ | R² | Position of Substituent on Pyrene Ring |
|---|---|---|---|---|
| 25 | 3,3'-dimethoxybiphenyl-4,4'-diyl | 3-methylphenyl | H | 1- |
| 26 | 3,3',5,5'-tetramethylbiphenyl-4,4'-diyl | 4-methylphenyl | H | 1- |
| 27 | 4,4'-oxydiphenyl | 3,4-dimethylphenyl | H | 1- |
| 28 | 4,4'-thiodiphenyl | 4-tert-butylphenyl | H | 1- |
| 29 | 4,4'-sulfonyldiphenyl | 4-(2-ethoxyethyl)phenyl | H | 1- |
| 30 | 4,4'-stilbenediyl (—C₆H₄—CH=CH—C₆H₄—) | 4-methylphenyl | H | 1- |
| 31 | —C₆H₄—CH=CH—C₆H₄—CH=CH—C₆H₄— | 3-propoxyphenyl | H | 1- |
| 32 | 4,4'-methylenediphenyl | 4-ethylphenyl | H | 1- |
| 33 | 2-methyl-2'-methyl-4,4'-(ethylene)diphenyl | 4-methylphenyl | H | 1- |
| 34 | p-terphenyl-4,4''-diyl | 3-methylphenyl | H | 1- |

TABLE 1-continued
| Compound No. | —(X)— | R¹ | R² | Position of Substituent on Pyrene Ring |
|---|---|---|---|---|
| 35 |  | 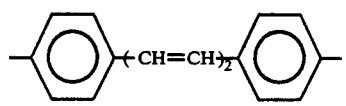 CH₃ | H | 1- |
| 36 | 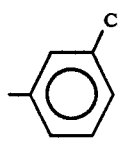 | 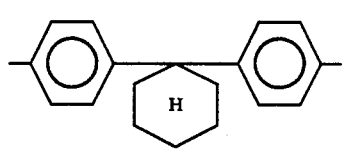 OCH₃ | H | 1- |
| 37 | 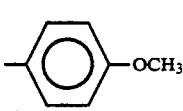 | 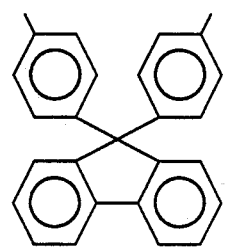 | H | 1- |
| 38 | 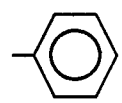 | 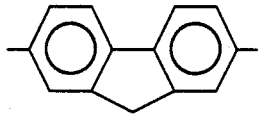 CH₃ | H | 1- |
| 39 | 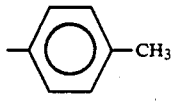 | —CH₂—  | H | 1- |
| 40 | 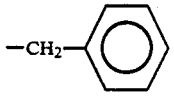 |  | H | 1- |
| 41 | 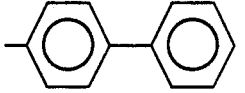 |  | 6-CH₃ | 1- |
| 42 | 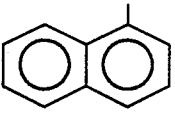 | 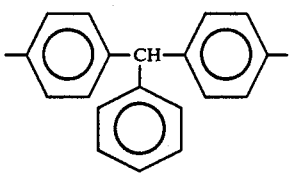 C₄H₉(n) | H | 1- |
| 43 | 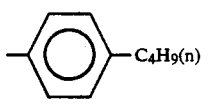 | 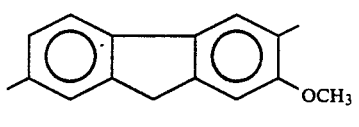 CH₃ | H | 1- |

TABLE 1-continued
| Compound No. | —⟨X⟩— | R¹ | R² | Position of Substituent on Pyrene Ring |
|---|---|---|---|---|
| 44 |  | 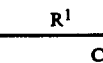 CH₃ | H | 1- |
| 45 | 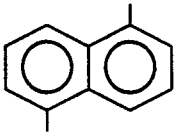 | 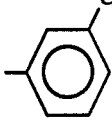 CH₃ | H | 1- |
| 46 | 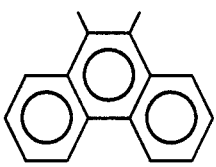 | 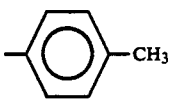 CH₃ | H | 1- |
| 47 | 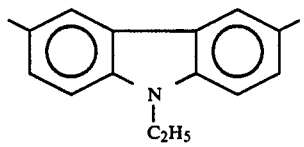 | 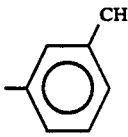 CH₃ | H | 1- |
| 48 | 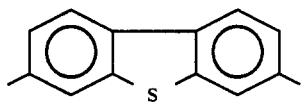 | 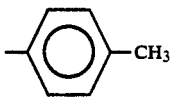 CH₃ | H | 1- |
| 49 | 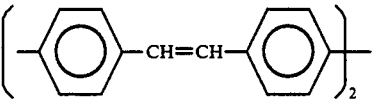 | 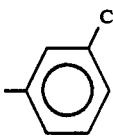 CH₃ | H | 1- |
| 50 | 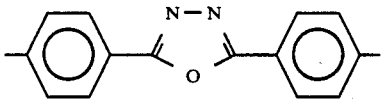 | 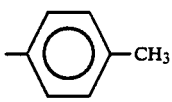 CH₃ | H | 1- |
| 51 | 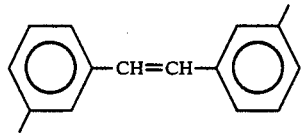 | 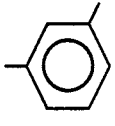 CH₃ | 3,6,8-tri-CH₃ | 1- |
| 52 | 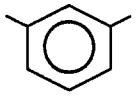 | 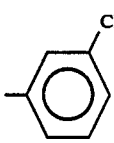 | H | 1- |
| 53 | 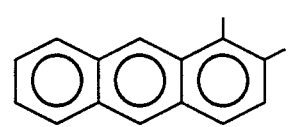 | 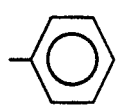 | H | 1- |

TABLE 1-continued
| Compound No. |  X | R[1] | R[2] | Position of Substituent on Pyrene Ring |
|---|---|---|---|---|
| 54 | 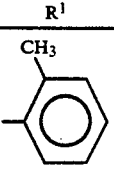 | 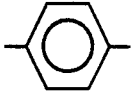 CH₃ | H | 1- |
| 55 | 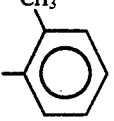 |  CH₃ | H | 1- |
| 56 | 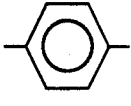 | 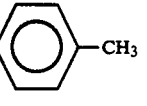 OCH₃ | H | 1- |
| 57 |  | 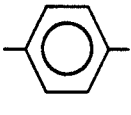 OCH₃ | H | 1- |
| 58 | 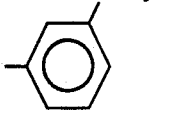 |  CH₃ | H | 1- |
| 59 | 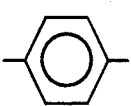 | 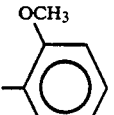 CH₃ | H | 1- |
| 60 |  | 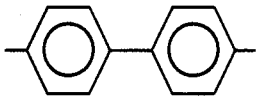 OCH₃ | H | 1- |
| 61 | 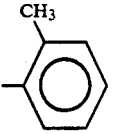 OCH₃ |  | H | 1- |
| 62 | 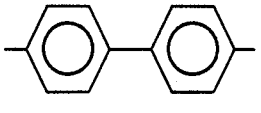 CH₃ CH₃ | 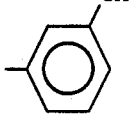 | H | 1- |
| 63 |  OCH₃ | —CH₂ | H | 1- |

TABLE 1-continued
| Compound No. | [ring with X] R¹ | R² | Position of Substituent on Pyrene Ring |
|---|---|---|---|
| 64 |  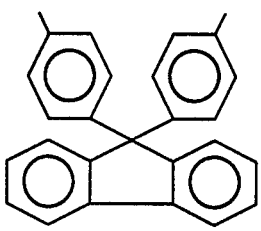 | H | 1- |
| 65 | 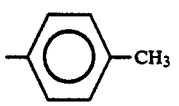 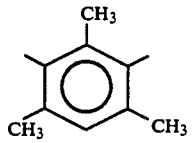 | H | 1- |
| 66 | 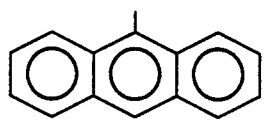 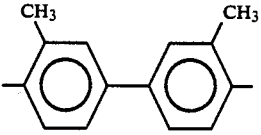 | H | 1- |
| 67 | 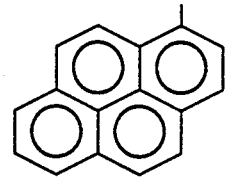 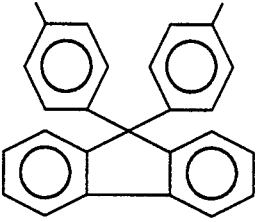 | 6-CH₃ | 1- |
| 68 | 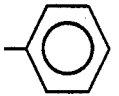 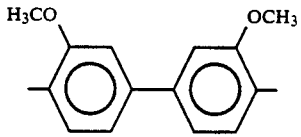 | H | 1- |
| 69 | 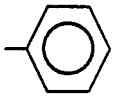 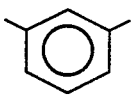 | H | 1- |
| 70 | 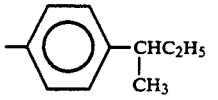 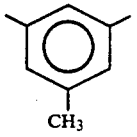 | H | 1- |
| 71 | 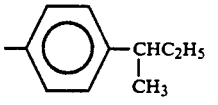 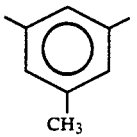 | H | 1- |

TABLE 1-continued

| Compound No. | —⟨X⟩— R¹ | R² | Position of Substituent on Pyrene Ring |
|---|---|---|---|
| 72 | 3,5-dimethylphenyl (CH₃ shown); R¹ = phenyl-CH(CH₃)(C₂H₅) | H | 1- |
| 73 | 3-methylphenyl; R¹ = 4-(n-C₄H₉)phenyl —⟨⟩—(CH₂)₃CH₃ | H | 1- |
| 74 | 3-methylphenyl; R¹ = 4-isobutylphenyl —⟨⟩—CH₂CH(CH₃)₂ | H | 1- |
| 75 | 3-methylphenyl; R¹ = 4-tert-butylphenyl —⟨⟩—C(CH₃)₃ | H | 1- |
| 76 | —⟨⟩—O—⟨⟩—; R¹ = —⟨⟩—CH₃ | H | 1- |
| 77 | —⟨⟩—S—⟨⟩—; R¹ = —⟨⟩—CH₃ | H | 1- |
| 78 | —⟨⟩—CH₂—⟨⟩—; R¹ = —⟨⟩—CH₃ | H | 1- |
| 79 | —⟨⟩—CH(cyclohexyl)—⟨⟩—; R¹ = —⟨⟩—CH₃ | H | 1- |
| 80 | 3,3'-dimethylbiphenyl-4,4'-diyl; R¹ = —⟨⟩—CH₃ | H | 1- |
| 81 | —⟨⟩—OCH₂CH₂O—⟨⟩—; R¹ = —⟨⟩—CH₃ | H | 1- |
| 82 | 3,3'-dimethylbiphenyl-4,4'-diyl; R¹ = —⟨⟩—OCH₃ | H | 1- |

TABLE 1-continued

| Compound No. | —(X)— | R¹ | R² | Position of Substituent on Pyrene Ring |
|---|---|---|---|---|
| 83 | —⌬—O(CH₂CH₂O)₂—⌬— | —⌬—CH₃ | H | 1- |
| 84 | —⌬—CH=CH—⌬—CH=CH—⌬— | —⌬—CH₃ | H | 1- |
| 85 | —⌬—CH=CH—⌬—CH=CH—⌬— | —⌬—⌬—CH₃ | H | 1- |
| 86 | —⌬—CH=CH—⌬—CH=CH—⌬— | —⌬— | H | 1- |
| 87 | —⌬—CH=CH—⌬—CH=CH—⌬— | —⌬—OCH₃ | H | 1- |

The diamine compounds of formula (I) for use in the electrophotographic photoconductor of the present invention are novel compounds and remarkably effective as photoconductive materials in the electrophotographic photoconductors. The diamine compounds are optically or chemically sensitized with a sensitizer such as a dye or a Lewis acid. Therefore, these compounds are usable as charge transporting materials when contained in a photoconductive layer of the electrophotographic photoconductor, especially of a function-separating type electrophotographic photoconductor comprising a charge generation layer which comprises an organic or inorganic pigment and a charge transport layer.

Among the above-mentioned diamine compounds, diamine compounds of formula (II) are more preferable:

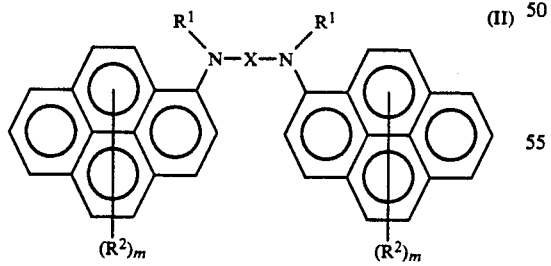

wherein $R^1$ represents an alkyl group having 1 to 4 carbon atoms, or an aryl group; $R^2$ represents hydrogen, an alkyl group having 1 to 4 carbon atoms, or an alkoxyl group having 1 to 4 carbon atoms; m is an integer of 1 or 2; and X represents a phenylene, biphenylene, fluorenediyl, or a group represented by

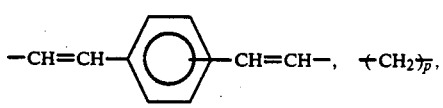

in which Y represents O, S, $-(CH=CH)_k-$, $-O(CH_2CH_2O)_q-$, $-CH=CH-\bigcirc-CH=CH-$, $-(CH_2)_p-$,

[cyclohexyl group], [fluorenyl group];

$R^3$ and $R^4$ each represent hydrogen, an having 1 to 4 carbon atoms, or an alkoxyl group having 1 to 4 carbon atoms; k and p each represent an integer of 1 to 2; and q represents an integer of 1 to 6.

To synthesize the above-mentioned diamine compound of formula (II), N-alkyl substitution reaction or N-aryl substitution reaction of a corresponding amino compound and N-pyrenyl substitution reaction are carried out stepwise using the respective corresponding halides. Conventionally, Ullmann reaction is employed for the aryl substitution reaction.

For example, the diamine compound of formula (I) for use in the electrophotographic photoconductor of the present invention can be prepared in the following manner:

An N,N'-diacetyl moiety of a diamino compound having formula (III) is allowed to react with a halide having formula (IV), so that the substitution is carried out at the both sites of nitrogen atoms:

$$H_2N-X-NH_2 \quad (III)$$

wherein X is the same as defined above.

$$R^1Z^1 \quad (IV)$$

wherein $R^1$ is the same as defined above; and $Z^1$ represents chlorine, bromine, or iodine.

The thus obtained condensate is subjected to hydrolysis, and condensed with a pyrenyl halide having formula (V) by the Ullmann reaction, so that the diamine compound having formula (I) of the present invention is obtained:

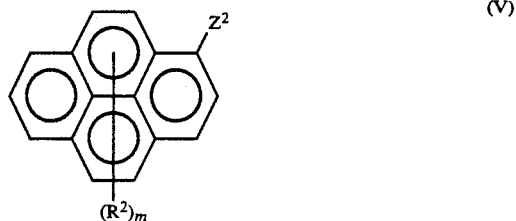

wherein $R^2$ and m are the same as defined above; and $Z^2$ represents bromine or iodine.

The diamine compound having formula (I) of the present invention can also be prepared by allowing the N,N'-diacetyl moiety of the diamino compound having formula (III) to react with the pyrenyl halide having formula (V), and subsequently allowing the above-obtained condensate to react with the halide having formula (IV).

In the case where $R^1$ in formula (IV) represents an alkyl group, a diamino compound having formula (III) also serves as a deoxidizer in the above-mentioned substitution reaction at the both sites of nitrogen atoms. Alternatively, other compounds such as organic amine, sodium hydrogencarbonate, potassium hydrogencarbonate, sodium carbonate, and potassium carbonate, which have high basicity as compared with the aforementioned diamino compound, may be used as the deoxidizer. This reaction is carried out in a polar solvent such as pyridine, acetone, tetrahydrofuran, methanol, or ethanol. The above reactions can also be carried out without a solvent.

In the case where Ullmann reaction is carried out using an aryl halide having formula (IV) or a pyrenyl halide having formula (V), N,N-dimethylformamide, nitrobenzene, dimethyl sulfoxide, or dichlorobenzene can be employed as a solvent. As the deoxidizer, basic compounds such as potassium carbonate, sodium carbonate, sodium hydrogen-carbonate, and hydrogenated sodium can be employed in this reaction. The above reaction is carried out at 160° to 250° C., in the presence of a solvent or without a solvent. When the reaction is not satisfactorily carried out under the above-mentioned conditions, it can be carried out in an autoclave at a temperature higher than the above-mentioned temperature range. Generally, the reaction can be satisfactorily carried out using a catalyst such as copper powder, copper oxide, or halogenated copper.

The structure of the photoconductor of the present invention will now be explained making reference to FIGS. 1 to 5.

In the photoconductors according to the present invention, one or more of diamine compounds of formula (I) are contained in the photoconductive layers 2, 2a, 2b, 2c and 2d. The diamine compounds can be employed in different ways, for example, as shown in FIGS. 1 to 5.

In the photoconductor shown in FIG. 1, a photoconductive layer 2 is formed on an electroconductive substrate 1, which photoconductive layer 2 comprises a diamine compound, a sensitizing dye and a binder agent (binder resin). In this photoconductor, the diamine compound works as a photoconductive material, through which charge carriers which are necessary for the light decay of the photoconductor are generated and transported. However, the diamine compound itself scarcely absorbs light in the visible light range, so that it is necessary to add a sensitizing dye which absorbs light in the visible light range in order to form latent electrostatic images by use of visible light.

Figure 2:
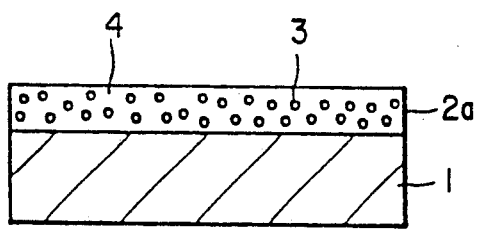
FIG. 2 is a schematic cross-sectional view of a second example of an electrophotographic photoconductor according to the present invention.

Referring to FIG. 2, there is shown a cross-sectional view of another embodiment of an electrophotographic photoconductor according to the present invention. In the figure, on the electroconductive substrate 1, there is formed a photoconductive layer 2a comprising a charge generating material 3 dispersed in a charge transporting medium 4 comprising a diamine compound and a binder agent. In this embodiment, the diamine compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is essential that the light-absorption wavelength regions of the charge generating material 3 and the diamine compound not overlap in the visible light range. This is because, in order to have the charge generating material 3 produce charge carriers efficiently, it is necessary to allow the light to reach the surface of the charge generating material 3. The diamine compounds of formula (I) scarcely absorb the light in the visible range. Therefore, especially when combined with the charge generating material 3 which absorbs the light in the visible region and generates charge carriers, the diamine compounds can work effectively as charge transporting materials.

Figure 3:
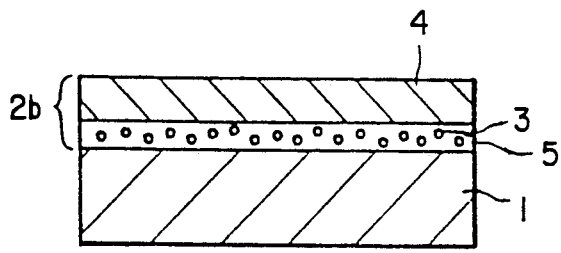
FIG. 3 is a schematic cross-sectional view of a third example of an electrophotographic photoconductor according to the present invention.

Referring to FIG. 3, there is shown a cross-sectional view of a further embodiment of an electrophotographic photoconductor according to the present invention. In the figure, there is formed on an electroconductive substrate 1 a two-layered photoconductive layer 2b comprising a charge generation layer 5 containing a charge generating material 3, and a charge transport layer 4 containing a diamine compound.

In this photoconductor, the light which has passed through the charge transport layer 4 reaches the charge generation layer 5, where charge carriers are generated. The charge carriers which are necessary for the light decay for latent electrostatic image formation are generated by the charge generating material 3, and accepted and transported by the charge transport layer 4.

In the charge transport layer 4, the diamine compound mainly works for transportation of the charge carriers. The generation and transportation of the charge carriers are performed in the same mechanism as that in the photoconductor shown in FIG. 2.

Figure 4:
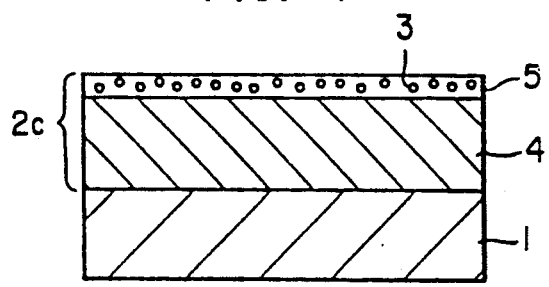
FIG. 4 is a schematic cross-sectional view of a fourth example of an electrophotographic photoconductor according to the present invention.

Referring to FIG. 4, there is shown still another embodiment of an electrophotographic photoconductor according to the present invention. In the figure, the overlaying order of a charge generation layer 5 and a charge transport layer 4 is reversed. The mechanism of the generation and transportation of charge carriers is the same as that of the photoconductor shown in FIG. 3.

Figure 5:
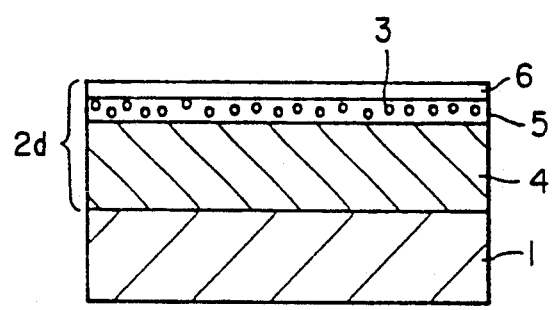
FIG. 5 is a schematic cross-sectional view of a fifth example of an electrophotographic photoconductor according to the present invention.

In the above photoconductor, a protective layer 6 may be formed on a charge generation layer 5 as shown in FIG. 5 for improving the mechanical strength thereof.

When the electrophotographic photoconductor according to the present invention shown in FIG. 1 is prepared, one or more of diamine compounds of formula (I) are dispersed in a binder resin solution, and a sensitizing dye is then added to the mixture, so that a photoconductive layer coating liquid is prepared. The thus prepared photoconductive layer coating liquid is coated on the electroconductive substrate 1 and dried, so that the photoconductive layer 2 is formed on the electroconductive substrate 1.

It is preferable that the thickness of the photoconductive layer 2 be in the range of 3 to 50 μm, more preferably in the range of 5 to 20 μm. It is preferable that the amount of the diamine compound contained in the photoconductive layer 2 be in the range of 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are as follows: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin B, Erythrosin, Rose Bengale and Fluoresccine; thiazine dyes such as Methylene Blue; cyanine dyes such as cyanin; and pyrylium dyes such as 2,6-diphenyl-4-(N,N-dimethylaminophenyl)thiapyrylium perchlorate and benzopyrylium salts (described in Japanese Patent Publication 48-25658). These sensitizing dyes can be used alone or in combination.

The electrophotographic photoconductor shown in FIG. 2 ca be obtained by dispersing finely-divided particles of the charge generating material 3 in the solution in which one or more of diamine compounds and the binder agent are dissolved, coating the above-prepared dispersion on the electroconductive substrate 1 and then drying the same to form the photoconductive layer 2a.

It is preferable that the thickness of the photoconductive layer 2a be in the range of 3 to 50 μm, more preferably in the range of 5 to 20 μm. It is preferable that the amount of the diamine compound contained in the photoconductive layer 2a be in the range of 10 to 95 wt. %, more preferably in the range of 30 to 90 wt. %.

It is preferable that the amount of the charge generating material 3 contained in the photoconductive layer 2a be in the range of 0.1 to 50 wt. %, more preferably in the range of 1 to 20 wt. %.

Specific examples of the charge generating material 3 are as follows: inorganic pigments such as selenium, selenium-tellurium, cadmium sulfide, cadmium sulfide-selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol scarlet B (made by Bayer Co., Ltd.) and Indanthrene Scarlet R (made by Bayer Co., Ltd.). These charge generating materials may be used alone or in combination.

The electrophotographic photoconductor shown in FIG. 3 can be obtained as follows:

The charge generating material 3 is vacuum-deposited on the electroconductive substrate 1, or the dispersion in which finely-divided particles of the charge generating material 3 are dispersed in an appropriate solvent, together with the binder agent when necessary, is coated on the electroconductive substrate 1 and dried, so that the charge generation layer 5 is formed. When necessary, the charge generation layer 5 is subjected to surface treatment by buffing and adjustment of the thickness thereof. On the thus formed charge generation layer 5, a coating liquid in which one or more of diamine compounds and the binder agent are dissolved is coated and dried, so that the charge transport layer 4 is formed. In the charge generation layer 5, the same charge generating material as employed in the previously mentioned photoconductive layer 2a can be used.

The thickness of the charge generation layer 5 is 5 μm or less, preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the diamine compound contained in the charge transport layer 4 be in the range of 10 to 95 wt. %, more preferably in the range of 30 to 90 wt. %.

The electrophotographic photoconductor shown in FIG. 4 can be obtained as follows:

A coating liquid in which the diamine compound and the binder agent are dissolved is coated on the electroconductive substrate 1 and dried to form the charge transport layer 4. On the thus formed charge transport layer 4, a dispersion prepared by dispersing finely-divided particles of the charge generating material 3 in the solvent, in which the binder agent is dissolved when necessary, is coated by spray coating and dried to form the charge generation layer 5 on the charge transport layer 4. The respective formulations of the charge generation layer and the charge transport layer are the same as previously described in FIG. 3.

The electrophotographic photoconductor shown in FIG. 5 can be obtained by forming the protective layer 6 on the charge generation layer 5 obtained in FIG. 4 by spray coating an appropriate resin solution. As a resin to be employed in the protective layer 6, any binder agents to be described later can be used.

Specific examples of materials for the electroconductive substrate 1 of the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl polymers such as polyvinylketone, polystyrene, poly-N-vinylcarbazole and polyacrylamide. All the resins having insulating properties and adhesive properties can be employed.

Some plasticizers may be added to the above-mentioned binder agent, when necessary. Examples of such plasticizers are halogenated paraffin, polybiphenyl chloride, dimethylnaphthalene and dibutyl phthalate.

Furthermore, in the electrophotographic photoconductors according to the present invention, an adhesive layer or a barrier layer can be interposed between the electroconductive substrate and the photoconductive layer when necessary. Examples of the material for use in the adhesive layer or the barrier layer are polyamide, nitrocellulose and aluminum oxide. It is preferable that the thickness of the adhesive layer or the barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image is transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

SYNTHESIS EXAMPLE 1

[Synthesis of N,N'-di(1-pyrenyl)-N,N'-bis(o-tolyl)-m-phenylenediamine (Compound No. 3)]

64.9 g (0.60 mol) of m-phenylenediamine was dissolved in 150 ml of glacial acetic acid. To this solution, 135 g (1.32 mol) of acetic anhydride was added dropwise at room temperature and the reaction was carried out at 60° C. for 1 hour.

After the completion of the reaction, 600 ml of water was poured into the above obtained reaction mixture, so that crystals separated out. These crystals were filtrated, washed with water, and dried, so that 109.6 g of N,N'-diacetyl-m-phenylenediamine was obtained in a 95.0% yield. The melting point of the above obtained product was 189.5 to 190.5° C. The IR spectrum of the product was measured with a commercially available infrared spectrophotometer (Trademark "IR-700", made by Jasco Corporation) by use of a KBr tablet. A characteristic band due to C=O was observed at 1660 cm$^{-1}$ ($\nu$C=O. 1660 cm$^{-1}$).

10 g (0.052 mol) of the above obtained N,N'-diacetyl-m-phenylenediamine, 26.8 g (0.12 mol) of -o-methyliodobenzene, 25.2 g (0.18 mol) of anhydrous potassium carbonate, 1.65 g (0.026 mol) of copper powder, and 10 ml of nitrobenzene were mixed and the reaction was carried out at 190° to 210° C. for 8 hours.

After the above obtained reaction mixture was cooled to room temperature, a solution prepared by dissolving 12.3 g (0.21 mol) of a 96% potassium hydroxide in a mixture of 80 ml of isoamyl alcohol and 20 ml of water was added to the reaction mixture. This mixture was subjected to hydrolysis at 125° C. for 5 hours. Isoamyl alcohol component was distilled away from the reaction mixture by steam distillation. After the resultant reaction product was extracted with 200 ml of toluene, insolubles were removed by filtration. The resultant product was washed with water, dried, and concentrated. The thus obtained crystals were washed with methanol and dried, so that 8.3 g of N,N'-bis(o-tolyl)-m-phenylenediamine was obtained in a 55.3% yield.

6.0 g (0.021 mol) of the above obtained N,N'-bis(o-tolyl)-m-phenylenediamine, 15.1 g (0.046 mol) of 1-iodopyrene, 10.8 g (0.078 mol) of anhydrous potassium carbonate, 1.3 g (0.02 mol) of copper powder, and 20 ml of nitrobenzene were mixed and the reaction was carried out at 200° to 210° C. for 24 hours.

After the completion of the reaction, 200 ml of toluene was added to the above obtained mixture. Insolubles were removed from the mixture by filtration, and the resultant product was washed with water, concentrated and evaporated to dryness.

The thus obtained crystals were subjected to column chromatography using a silica gel as a carrier and a mixed solvent of toluene and hexane at a ratio of 1:2 as an eluting solution, whereby 7.9 g of N,N'-di(1-pyrenyl)-N,N'-bis(o-tolyl)-m-phenylenediamine (Compound No. 3) was obtained in a 54.6% yield.

The melting point of the above obtained compound was 263.5° to 264.5° C. The results of the elemental analysis of the compound were as follows:

|  | % C | % H | % N |
|---|---|---|---|
| Calculated | 90.67 | 5.27 | 4.07 |
| Found | 90.60 | 5.48 | 4.11 |

The above calculation was based on the formula for N,N'-di(1-pyrenyl -N,N'-bis(o-tolyl)-m-phenylenediamine of $C_{52}H_{36}N_2$.

Figure 6:
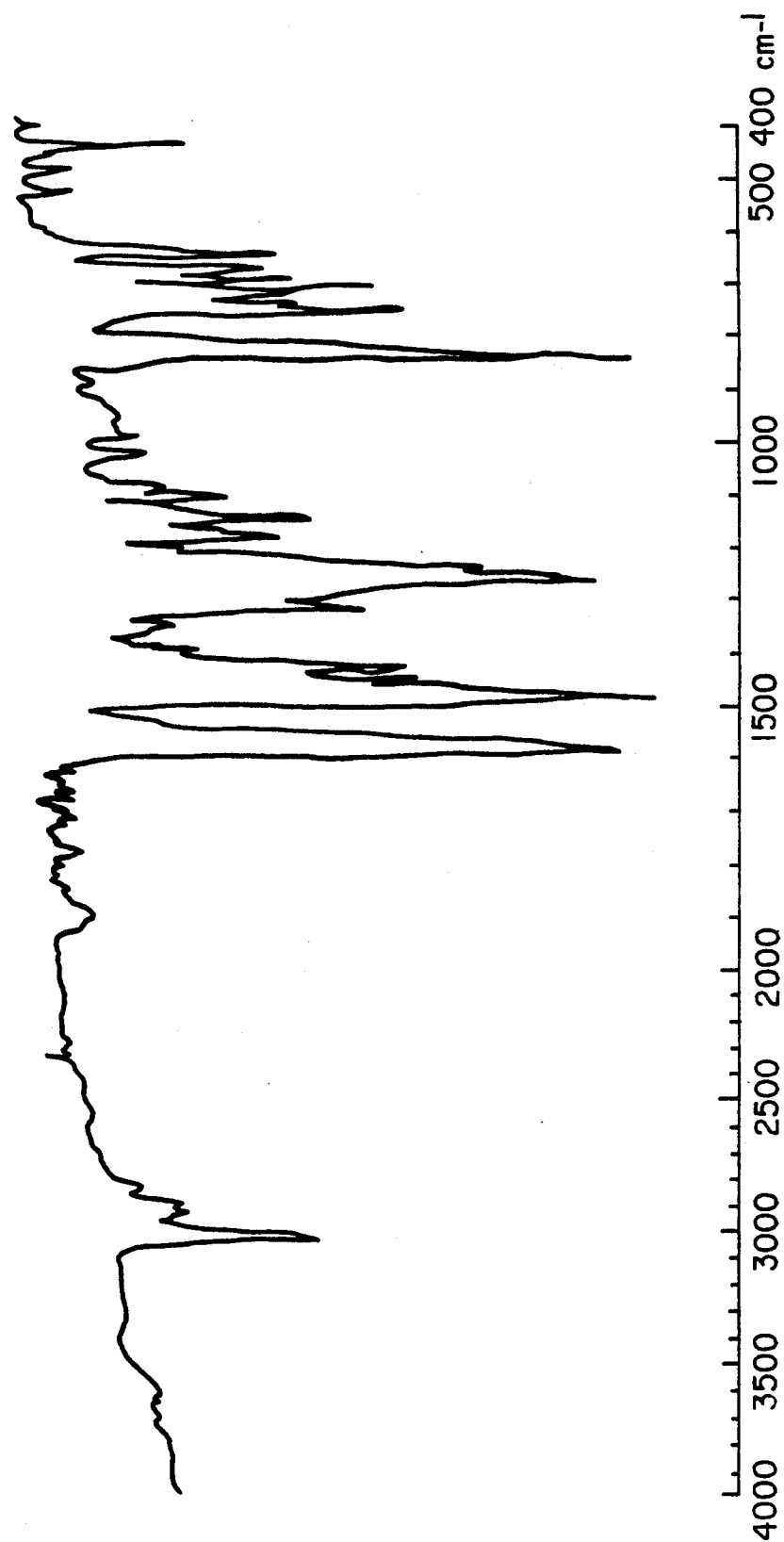
FIG. 6 is an IR spectrum of N,N'-di(1-pyrenyl)-N,N'-bis(o-tolyl)-m-phenylenediamine obtained in Synthesis Example 1.

FIG. 6 shows an IR spectrum of the above compound taken by use of a KBr tablet.

SYNTHESIS EXAMPLE 2

[Synthesis of
N,N'-bis(o-methoxyphenyl)-N,N'-di(1-pyrenyl)-m-phenylenediamine]

The N,N'-diacetyl-m-phenylenediamine was obtained in the same manner as in Synthesis Example 1.

10 g (0.052 mol) of the above obtained N,N'-diacetyl-m-phenylenediamine, 29.2 g (0.11 mol) of o-methoxyiodobenzene, 25.2 g (0.18 mol) of anhydrous potassium carbonate, 1.65 g (0.026 mol) of copper powder, and 10 ml of nitrobenzene were mixed and the reaction was carried out at 180° to 200° C. for 10 hours.

After the above obtained reaction mixture was cooled to room temperature, a solution prepared by dissolving 12.3 g (0.21 mol) of a 96% potassium hydroxide in a mixture of 80 ml of isoamyl alcohol and 20 ml of water was added to the reaction mixture. This mixture was subjected to hydrolysis at 125° C. for 5 hours. Isoamyl alcohol component was distilled away from the reaction mixture by steam distillation. After the resultant reaction product was extracted with 200 ml of toluene, insolubles were removed by filtration. The resultant product was washed with water, dried, and concentrated. The thus obtained crystals were washed with methanol and dried, so that 9.3 g of N,N'-bis(o-methoxyphenyl)-m-phenylenediamine was obtained in a 58.0% yield.

6.9 g (0.021 mol) of the above obtained N,N'-bis(o-methoxyphenyl)-m-phenylenediamine, 15.1 g (0.046 mol) of 1-iodopyrene, 10.8 g (0.078 mol) of anhydrous potassium carbonate, 1.3 g (0.02 mol) of copper powder, and 20 ml of nitrobenzene were mixed and the reaction was carried out at 200° to 210° C. for 24 hours.

After the completion of the reaction, 200 ml of toluene was added to the above obtained mixture. Insolubles were removed from the mixture by filtration, and the resultant product was washed with water, concentrated and evaporated to dryness.

The thus obtained crystals were subjected to column chromatography using a silica gel as a carrier, and a mixed solvent of toluene and hexane at a ratio of 2:1 as an eluting solution, whereby 7.1 g of N,N'-bis(o-methoxyphenyl)-N,N'-di(1-pyrenyl)-m-phenylenediamine was obtained in a 46.9% yield.

The melting point of the above obtained compound was 244.0° to 245.0° C. The results of the elemental analysis of the compound were as follows:

|  | % C | % H | % N |
|---|---|---|---|
| Calculated | 86.64 | 5.03 | 3.89 |
| Found | 86.50 | 5.29 | 3.67 |

The above calculation was based on the formula for N,N'-bis(o-methoxyphenyl)-N,N'-di(1-pyrenyl)-m-phenylenediamine of $C_{52}H_{36}N_2O_2$.

SYNTHESIS EXAMPLE 3

[Synthesis of
N,N'-bis(3,4-dimethylphenyl)-N,N'-di(1-pyrenyl)-m-phenylenediamine]

The N,N'-diacetyl-m-phenylenediamine was obtained in the same manner as in Synthesis Example 1.

10 g (0.052 mol) of the above obtained N,N'-diacetyl-m-phenylenediamine, 21.2 g (0.11 mol) of 3,4-dimethylbromobenzene, 25.2 g (0.18 mol) of anhydrous potassium carbonate, 1.65 g (0.026 mol) of copper powder, and 10 ml of nitrobenzene were mixed and the reaction was carried out at 180° to 190° C. for 20 hours.

After the above obtained reaction mixture was cooled to room temperature, a solution prepared by dissolving 12.3 g (0.21 mol) of a 96% potassium hydroxide in a mixture of 80 ml of isoamyl alcohol and 20 ml of water was added to the reaction mixture. This mixture was subjected to hydrolysis at 125° C. for 8 hours. Isoamyl alcohol component was distilled away from the reaction mixture by steam distillation. After the resultant reaction product was extracted with 200 ml of toluene, insolubles were removed by filtration. The resultant product was washed with water, dried, and concentrated. The thus obtained crystals were washed with methanol and dried, so that 10.7 g of N,N'-bis(3,4-dimethylphenyl)-m-phenylenediamine was obtained in a 64.8% yield.

8.0 g (0.025 mol) of the above obtained N,N'-bis(3,4-dimethylphenyl)-m-phenylenediamine, 18.0 g (0.055 mol) of 1-iodopyrene, 15.0 g (0.108 mol) of anhydrous potassium carbonate, 1.6 g (0.025 mol) of copper powder, and 20 ml of nitrobenzene were mixed and the reaction was carried out at 180° to 200° C. for 15 hours.

After the completion of the reaction, 200 ml of toluene was added to the above obtained mixture. Insolubles were removed from the mixture by filtration, and the resultant product was washed with water, concentrated and evaporated to dryness.

The thus obtained crystals were subjected to column chromatography using a silica gel as a carrier, and a mixed solvent of toluene and hexane at a ratio of 1:2 as an eluting solution, whereby 8.6 g of N,N'-bis(3,4-dimethylphenyl)-N,N'-di(1-pyrenyl)-m-phenylenediamine was obtained in a 48.0% yield.

The melting point of the above obtained compound was 243.0° to 245.0° C. The results of the elemental analysis of the compound were as follows:

|  | % C | % H | % N |
|---|---|---|---|
| Calculated | 90.47 | 5.62 | 3.91 |
| Found | 90.71 | 5.85 | 3.68 |

The above calculation was based on the formula for N,N'-bis(3,4-dimethylphenyl)-N,N'-di(1-pyrenyl)-m-phenylenediamine of $C_{54}H_{40}N_2$.

SYNTHESIS EXAMPLES 4 AND 5

[Synthesis of
N,N'-di(1-pyrenyl)-N,N'-bis(m-tolyl-)-m-phenylenediamine and
N,N'-di(1-pyrenyl)-N,N'-bis(p-tolyl)-m-phenylenediamine]

The procedure for preparing N,N'-di(1-pyrenyl)-N,N'-bis(o-tolyl)-m-phenylenediamine in Synthesis Example 1 was repeated except that o-methyliodobenzene employed in Synthesis Example 1 was respectively replaced by m-methyliodobenzene and p-methyliodobenzene, whereby N,N'-di(1-pyrenyl)-N,N'-bis(m-tolyl-m-phenylenediamine and N,N'-di(1-pyrenyl)-N,N'-bis(p-tolyl)-m-phenylenediamine were obtained.

The melting points and the results of the elemental analysis of the above obtained compounds are shown in Table 2.

SYNTHETIC EXAMPLES 6 AND 7

[Synthesis of
N,N'-bis(m-methoxyphenyl)-N,N'-di(1-pyrenyl)-m-phenylenediamine and
N,N'-bis(p-methoxyphenyl)-N,N'-di(1-pyrenyl)-m-phenylenediamine]

The procedure for preparing N,N'-bis(o-methoxyphenyl)-N,N'-di(1-pyrenyl)-m-phenylenediamine in Synthesis Example 2 was repeated except that o-methoxyiodobenzene employed in Synthesis Example 2 was respectively replaced by m-methoxyiodobenzene and p-methoxyiodobenzene, whereby N,N'-bis(m-methoxyphenyl)-N,N'-di(1-pyrenyl)-m-phenylenediamine and N,N'-bis(p-methoxyphenyl)-N,N'-di(1-pyrenyl)-m-phenylenediamine were obtained.

The melting points and the results of the elemental analysis of the above obtained compounds are shown in Table 2.

SYNTHESIS EXAMPLE 8

[Synthesis of
N,N'-bis(3,4-dimethoxyphenyl)-N,N'-di(1-pyrenyl)-m-phenylenediamine]

The procedure for preparing N,N'-bis(3,4-dimethylphenyl)-N,N'-di(1-pyrenyl)-m-phenylenediamine in Synthesis Example 3 was repeated except that 21.2 g of 3,4-dimethylbromobenzene employed in Synthesis Example 3 was replaced by 23.9 g of 3,4-dimethoxybromobenzene, whereby N,N'-bis(3,4-dimethoxyphenyl)-N,N'-di(1-pyrenyl)-m-phenylenediamine was obtained.

The melting point and the results of the elemental analysis of the above obtained compound are shown in Table 2.

SYNTHESIS EXAMPLES 9 TO 26

The procedure for preparing N,N'-di(1-pyrenyl)-N,N'-bis(o-tolyl)-m-phenylenediamine in Synthesis Example 1 was repeated except that N,N'-diacetyl-m-phenylenediamine, o-methyliodobenzene, and 1-iodopyrene employed in Synthesis Example 1 were respectively replaced by each of N,N'-diacetyl moieties of formula (III), halides of formula (IV), and pyrenyl halides of formula (V-a) having X and $R^1$ shown in Table 2, whereby diamine compounds of formula (II-a) were obtained. The melting points and the results of the elemental analysis of the above obtained compounds are also shown in Table 2.

wherein $Z^1$ represents chlorine, bromine, or iodine.

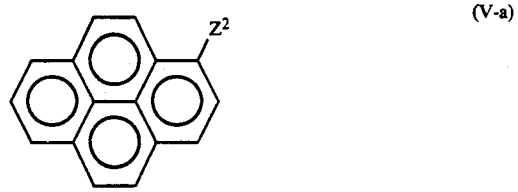

wherein $Z^2$ represents bromine or iodine.

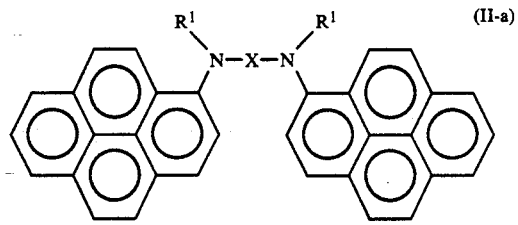

TABLE 2
| Synthesis Ex. No. | Compound No. in Table 1 | X | R¹ | Melting Point (°C.) | Elemental Analysis Found (Calculated) | | |
|---|---|---|---|---|---|---|---|
| | | | | | % C | % H | % N |
| Ex. 4 | 4 | 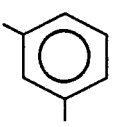 | 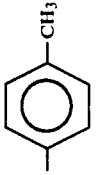 (CH₃) | 233.0–234.5 | 90.29 (90.67) | 5.54 (5.27) | 4.29 (4.07) |
| Ex. 5 | 5 | 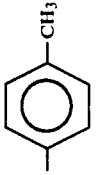 | 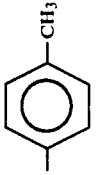 (CH₃) | 267.5–268.5 | 90.85 (90.67) | 5.51 (5.27) | 3.97 (4.07) |
| Ex. 6 | 7 | 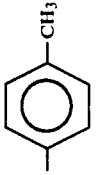 | 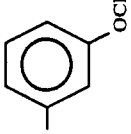 (OCH₃) | 190.5–192.0 | 86.39 (86.64) | 5.34 (5.03) | 3.71 (3.89) |
| Ex. 7 | 8 | 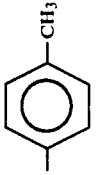 | 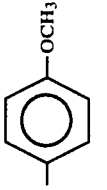 (OCH₃) | 246.0–247.0 | 86.85 (86.64) | 5.22 (5.03) | 3.82 (3.89) |
| Ex. 8 | 10 | 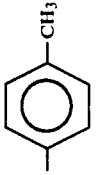 | 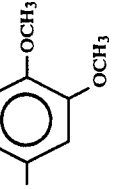 (OCH₃, OCH₃) | 210.5–212.0 | 83.42 (83.05) | 5.39 (5.16) | 3.76 (3.59) |
| Ex. 9 | 69 | 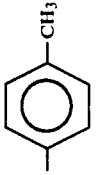 | 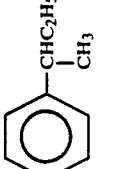 (CHC₂H₅, CH₃) | 207.5–209.0 | 89.51 (90.12) | 6.30 (6.26) | 3.10 (3.62) |
| Ex. 10 | 73 | 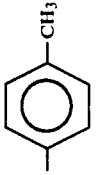 | 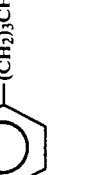 ((CH₂)₃CH₃) | 153.0–158.0 | 89.91 (90.12) | 6.33 (6.26) | 3.58 (3.62) |

TABLE 2-continued

| Synthesis Ex. No. | Compound No. in Table 1 | X | R¹ | Melting Point (°C.) | Elemental Analysis Found (Calculated) | | |
|---|---|---|---|---|---|---|---|
| | | | | | % C | % H | % N |
| Ex. 11 | 74 | 4-methylphenyl | 4-(isobutyl)phenyl (CH₂CH(CH₃)₂) | 179.5–183.5 | 89.40 (90.12) | 6.30 (6.26) | 3.10 (3.62) |
| Ex. 12 | 75 | 4-methylphenyl | 4-(tert-butyl)phenyl C(CH₃)₃ | 199.0–201.5 | 90.10 (90.12) | 6.20 (6.26) | 3.10 (3.62) |
| Ex. 13 | 1 | 4-methylphenyl | —C₂H₅ | 111.0–115.0 | 89.40 (89.32) | 5.51 (5.72) | 5.10 (4.96) |
| Ex. 14 | 70 | 3,5-dimethylphenyl | 4-(sec-butyl)phenyl CHC₂H₅/CH₃ | 237.0–238.0 | 89.46 (90.04) | 6.48 (6.40) | 3.13 (3.56) |
| Ex. 15 | 24 | 4,4'-dimethylbiphenyl | 4-methylphenyl | >300 | 90.29 (91.07) | 5.42 (5.27) | 3.33 (3.66) |
| Ex. 16 | 76 | bis(4-methylphenyl) ether | 4-methylphenyl | 200.0–201.0 | 88.40 (89.20) | 5.21 (5.16) | 3.25 (3.59) |
| Ex. 17 | 77 | bis(4-methylphenyl) sulfide | 4-methylphenyl | 198.0–200.0 | 87.09 (87.40) | 5.18 (5.06) | 3.28 (3.51) |

TABLE 2-continued

| Synthesis Ex. No. | Compound No. in Table 1 | X | R¹ | Melting Point (°C.) | Elemental Analysis Found (Calculated) | | |
|---|---|---|---|---|---|---|---|
| | | | | | % C | % H | % N |
| Ex. 18 | 78 | (4,4'-dimethylbenzhydryl-CH₂-) | p-tolyl | 181.5–188.0 | 90.97 (90.97) | 5.62 (5.43) | 3.50 (3.60) |
| Ex. 19 | 79 | (bis(4-methylphenyl)cyclohexyl, H) | p-tolyl | 185.0–195.2 | 90.77 (90.74) | 6.07 (5.95) | 3.28 (3.31) |
| Ex. 20 | 64 | (9,9-bis(4-methylphenyl)fluorene) | p-tolyl | 283.0–285.0 | 91.58 (91.77) | 5.17 (5.22) | 3.24 (3.02) |
| Ex. 21 | 81 | (bis(4-methylphenyl)-OCH₂CH₂O-) | p-methoxyphenyl | 219.0–222.5 | 87.00 (87.35) | 5.45 (5.38) | 3.10 (3.40) |
| Ex. 22 | 82 | (3,3'-dimethylbiphenyl-dimethyl) | p-tolyl | 309 | 87.18 (87.35) | 5.63 (5.38) | 3.20 (3.40) |
| Ex. 23 | 80 | (3,3'-dimethylbiphenyl-dimethyl) | p-tolyl | amorphous | 90.75 (90.90) | 5.61 (5.59) | 3.28 (3.53) |

TABLE 2-continued
| Synthesis Ex. No. | Compound No. in Table 1 | X | R¹ | Melting Point (°C.) | Elemental Analysis Found (Calculated) | | |
|---|---|---|---|---|---|---|---|
| | | | | | % C | % H | % N |
| Ex. 24 | 83 |  |  | amorphous | 85.41 (85.69) | 5.31 (5.57) | 3.32 (3.22) |
| Ex. 25 | 84 | 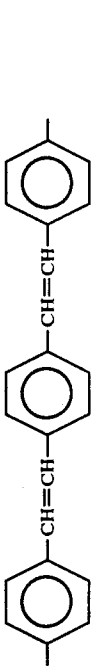 |  | >280 | 91.52 (91.45) | 5.31 (5.42) | 3.12 (3.14) |
| Ex. 26 | 85 | 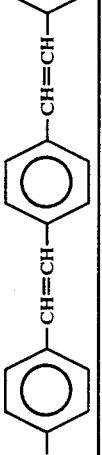 |  | 240 | 91.90 (91.92) | 5.13 (5.40) | 2.51 (2.68) |

EXAMPLE 1

76 parts by weight of Diane Blue (C.I. Pigment Blue 25:C.I. 21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

2 parts by weight of a diamine compound (Compound No. 9) serving as a charge transporting material, 2 parts by weight of polycarbonate resin (Trademark "Panlite K-1300" made by Teijin Limited) and 16 parts by weight of tetrahydrofuran were mixed to prepare a coating liquid for a charge transport layer. This liquid was coated on the above formed charge generation layer by a doctor blade, and dried at 80° C. for 2 minutes and then at 120° C. for 5 minutes, so that a charge transport layer with a thickness of about 20 μm was formed on the charge generation layer. Thus an electrophotographic photoconductor No. 1 according to the present invention was prepared.

EXAMPLES 2 TO 42

The procedure for preparing the electrophotographic photoconductor No. 1 in Example 1 was repeated except that Diane Blue serving as a charge generating material for use in the charge generation layer and the Compound No. 9 serving as a charge transporting material for use in the charge transport layer in Example 1 were respectively replaced by each of the charge generating materials and charge transporting materials listed in the following Table 3, whereby electrophotographic photoconductors No. 2 to No. 42 according to the present invention were prepared.

TABLE 3

| Photo-conductor No. | Charge Generating Material | Charge Transporting Material (Diamine Compound No.) |
|---|---|---|
| 1 | (bis-azo naphthol structure with OCH₃ substituents and phenyl CONH groups) | 9 |
| 2 | (bis-azo naphthol structure with Cl substituents and phenyl CONH groups) | 9 |
| 3 | (bis-azo naphthol structure with distyrylbenzene central unit and 2,4-dimethylphenyl CONH groups) (hereinafter referred to as P-1) | 9 |

TABLE 3-continued

| Photo-conductor No. | Charge Generating Material | Charge Transporting Material (Diamine Compound No.) |
|---|---|---|
| 4 | | 9 |
| 5 | (hereinafter referred to as P-2) | 9 |
| 6 | | 9 |
| 7 | (hereinafter referred to as P-3) β-type Copper Phthalocyanine | 9 |

TABLE 3-continued

| Photo-conductor No. | Charge Generating Material | | Charge Transporting Material (Diamine Compound No.) |
|---|---|---|---|
| 8 | (structure: naphthalene with CONH-phenyl, OH, N=N-phenyl(OCH₃)-phenyl(H₃CO)-N=N-naphthalene(OH)(CONH-phenyl)) | | 7 |
| 9 | (structure: naphthalene with CONH-phenyl, OH, N=N-phenyl(Cl)-phenyl(Cl)-N=N-naphthalene(OH)(CONH-phenyl)) | | 7 |
| 10 | | P-1 | 7 |
| 11 | | P-2 | 7 |
| 12 | | P-3 | 7 |
| 13 | | P-1 | 8 |
| 14 | | P-2 | 8 |
| 15 | | P-3 | 8 |
| 16 | | P-2 | 64 |
| 17 | | P-3 | 64 |
| 18 | | P-2 | 69 |
| 19 | | P-3 | 69 |
| 20 | | P-2 | 73 |
| 21 | | P-3 | 73 |
| 22 | | P-2 | 74 |
| 23 | | P-3 | 74 |
| 24 | | P-2 | 75 |
| 25 | | P-3 | 75 |
| 26 | | P-2 | 76 |
| 27 | | P-3 | 76 |
| 28 | | P-2 | 77 |
| 29 | | P-3 | 77 |

TABLE 3-continued

| Photo-conductor No. | Charge Generating Material | Charge Transporting Material (Diamine Compound No.) |
|---|---|---|
| 30 | P-2 | 78 |
| 31 | P-3 | 78 |
| 32 | P-2 | 79 |
| 33 | P-3 | 79 |
| 34 | P-2 | 1 |
| 35 | P-2 | 80 |
| 36 | P-3 | 80 |
| 37 | P-2 | 81 |
| 38 | P-2 | 81 |
| 39 | P-3 | 82 |
| 40 | P-2 | 82 |
| 41 | P-2 | 83 |
| 42 | P-3 | 83 |

EXAMPLE 43

Selenium was vacuum-deposited on an aluminum plate with a thickness of about 300 μm, so that a charge generation layer with a thickness of about 1 μm was formed on the aluminum plate.

2 parts by weight of the Compound No. 9, 3 parts by weight of polyester resin (Trademark "Polyester Adhesive 49000" made by Du Pont de Nemours, E. I. & Co.) and 45 parts by weight of tetrahydrofuran were mixed to prepare a coating liquid for a charge transport layer. This liquid was coated on the above formed charge generation layer by a doctor blade, and dried at room temperature and then under reduced pressure, so that a charge transport layer with a thickness of about 10 μm was formed on the charge generation layer. Thus an electrophotographic photoconductor No. 43 according to the present invention was prepared.

EXAMPLE 44

The procedure for preparing the electrophotographic photoconductor No. 43 in Example 43 was repeated except that a charge generation layer with a thickness of about 0.6 μm was formed on the same aluminum plate as employed in Example 43 by deposition of the following perylene pigment instead of selenium, so that an electrophotographic photoconductor No. 44 according to the present invention was prepared:

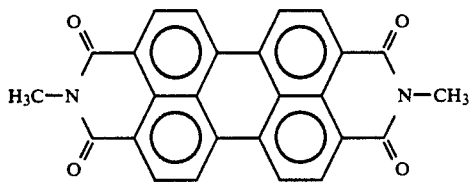

EXAMPLE 45

1 part by weight of the same Diane Blue as employed in Example 1 and 158 parts by weight of tetrahydrofuran were mixed and ground in a ball mill to prepare a dispersion. To the thus prepared dispersion, 12 parts by weight of the Compound No. 9 and 18 parts by weight of polyester resin (Trademark Polyester Adhesive 49000" made by Du Pont de Nemours, E. I. & Co.) were added to prepare a coating liquid for a photoconductive layer. This liquid was coated on an aluminum-deposited polyester film serving as an electroconductive substrate by a doctor blade, and dried at 100° C. for 30 minutes, so that a photoconductive layer with a thickness of about 16 μm was formed on the electroconductive substrate. Thus, an electrophotographic photoconductor No. 45 according to the present invention was prepared.

EXAMPLE 46

2 parts by weight of the Compound No. 9 serving as a charge transporting material, 2 parts by weight of polycarbonate resin (Trademark "Panlite K-1300" made by Teijin Limited) and 16 parts by weight of tetrahydrofuran were mixed to prepare a coating liquid for a charge transport layer. This liquid was coated on an aluminum-deposited polyester film serving as an electroconductive substrate by a doctor blade, and dried at 80° C. for 2 minutes and then at 120° C. for 5 minutes, so that a charge transport layer with a thickness of about 20 μm was formed on the electroconductive substrate.

13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve were mixed and ground in a ball mill to prepare a dispersion. To this dispersion, 1700 parts by weight of ethyl cellosolve were further added and stirred to prepare a coating liquid for a charge generation layer. This liquid was coated on the above formed charge transport layer by spray coating and dried at 100° C. for 10 minutes, so that a charge generation layer with a thickness of about 0.2 μm was formed on the charge transport layer.

A methanol/n-butanol solution of a polyamide resin (Trademark "CM-8000" made by Toray Industries, Inc.) was coated on the above formed charge generation layer by spray coating and dried at 120° C. for 30 minutes, so that a protective layer with a thickness of about 0.5 μm was formed on the charge generation layer. Thus, an electrophotographic photoconductor No. 46 according to the present invention was prepared.

Each of the thus prepared electrophotographic photoconductors No. 1 to No. 46 according to the present invention was charged under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lap in such a manner that the illuminance on the illuminated surface of the photoconductor was 4.5 lux, and the exposure $E_{\frac{1}{2}}$ (lux·sec) required to reduce the initial surface potential Vpo (V) to ½ thereof was measured. The results are shown in Table 4.

Furthermore, each of the electrophotographic photoconductors No. 1 to No. 46 according to the present invention was charged by use of a commercially available electrophotographic copying machine. Then a latent electrostatic image was formed on the photoconductor using an original by illuminating the charged photoconductor. The thus formed latent electrostatic image was developed by a dry-type developer to a visible image. The thus obtained toner image was electrostatically transferred and fixed onto a sheet of normal paper, so that a clear transferred image was obtained. A clear image was also obtained when a wet-type developer was employed for development of the latent electrostatic image.

TABLE 4

| Photoconductor No. | Vpo (V) | $E_{\frac{1}{2}}$ (lux · sec) |
|---|---|---|
| 1 | −1200 | 2.01 |
| 2 | −970 | 1.72 |
| 3 | −1340 | 0.61 |
| 4 | −1120 | 1.90 |
| 5 | −1028 | 0.80 |
| 6 | −1013 | 0.52 |
| 7 | −750 | 0.65 |
| 8 | −1110 | 1.20 |
| 9 | −980 | 1.71 |
| 10 | −1220 | 0.92 |
| 11 | −1501 | 1.01 |
| 12 | −925 | 0.67 |
| 13 | −620 | 0.62 |

TABLE 4-continued

| Photoconductor No. | Vpo (V) | $E_{\frac{1}{2}}$ (lux · sec) |
|---|---|---|
| 14 | −394 | 0.98 |
| 15 | −530 | 0.48 |
| 16 | −1286 | 1.30 |
| 17 | −1343 | 1.34 |
| 18 | −1303 | 1.00 |
| 19 | −1081 | 0.59 |
| 20 | −1117 | 1.21 |
| 21 | −1025 | 0.77 |
| 22 | −1323 | 1.03 |
| 23 | −1097 | 0.66 |
| 24 | −1195 | 1.03 |
| 25 | −1049 | 0.67 |
| 26 | −1393 | 1.16 |
| 27 | −1099 | 0.74 |
| 28 | −1197 | 1.04 |
| 29 | −1096 | 0.75 |
| 30 | −1226 | 1.08 |
| 31 | −1157 | 0.72 |
| 32 | −1245 | 1.03 |
| 33 | −1119 | 0.65 |
| 34 | −1369 | 1.79 |
| 35 | −1128 | 0.83 |
| 36 | −990 | 0.51 |
| 37 | −1089 | 0.96 |
| 38 | −910 | 0.55 |
| 39 | −1020 | 0.72 |
| 40 | −870 | 0.47 |
| 41 | −1205 | 0.87 |
| 42 | −1010 | 0.50 |
| 43 | −1320 | 2.42 |
| 44 | −1410 | 3.15 |
| 45 | +1100 | 1.51 |
| 46 | +1230 | 0.70 |

The electrophotographic photoconductors of the present invention exhibit a significantly improved resistance to heat and mechanical shocks as well as excellent photoconductive properties. Furthermore, the photoconductors according to the present invention can be manufactured at a low cost.

The diamine compounds of the present invention for use in the electrophotographic photoconductor are novel compounds and remarkably effective as photoconductive materials in the electrophotographic photoconductor.

What is claimed is:

1. An electrophotographic photoconductor comprising an electroconductive substrate and a photoconductive layer formed thereon comprising a diamine compound of formula (I):

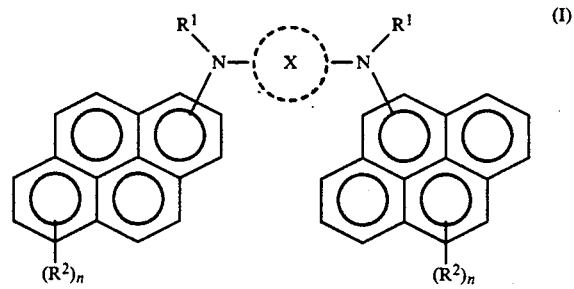

wherein $R^1$ is an alkyl group having 1 to 4 carbon atoms, or an aryl group; $R^2$ is hydrogen, an alkyl group having 1 to 4 carbon atoms, or an alkoxy group having 1 to 4 carbon atoms; n is an integer of 1 to 3; and

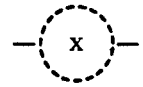

is an arylene group or a bivalent group of a heterocyclic compound, said photoconductive layer comprising said diamine compound, a sensitizer dye and a binder, or said photoconductive layer comprising a charge generating material and a charge transporting material which comprises said diamine compound and a binder.

2. The electrophotographic photoconductor as claimed in claim 1, wherein $R^1$ is a non-condensed hydrocarbon group.

3. The electrophotographic photoconductor as claimed in claim 2, wherein $R^1$ is selected from the group consisting of phenyl group, biphenyl group, and terphenyl group.

4. The electrophotographic photoconductor as claimed in claim 1, wherein $R^1$ is a condensed polycyclic hydrocarbon group having not more than 18 carbon atoms in a ring thereof.

5. The electrophotographic photoconductor as claimed in claim 4, wherein $R^1$ is selected from the group consisting of pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

6. The electrophotographic photoconductor as claimed in claim 1, wherein $R^1$ has a substituent selected from the group consisting of a halogen atom, a cyano group, a nitro group, an alkyl group having 1 to 12 carbon atoms, an alkoxyl group represented by $-OR^5$, in which $R^5$ is an alkyl group having 1 to 12 carbon atoms, an aryloxy group with an aryl group selected from the group consisting of phenyl group and naphthyl group, a substituted mercapto group represented by $-SR^6$, in which $R^6$ is an alkyl group having 1 to 12 carbon atoms or an aryl group selected from the group consisting of a non-condensed hydrocarbon group and a condensed polycyclic hydrocarbon group, a group

in which $R^7$ and $R^8$ each is hydrogen, an alkyl group having 1 to 12 carbon atoms, or an aryl group selected from the group consisting of phenyl group, biphenyl group, and naphthyl group, an alkylenedioxy group, and an alkylenedithio group.

7. The electrophotographic photoconductor as claimed in claim 1, wherein

is a bivalent group of a monocyclic hydrocarbon compound.

8. The electrophotographic photoconductor as claimed in claim 7, wherein said monocyclic hydrocarbon compound is selected from the group consisting of benzene, diphenyl ether, polyethylene glycol diphenyl ether, diphenyl thioether, and diphenyl sulfone.

9. The electrophotographic photoconductor as claimed in claim 1, wherein

is a bivalent group of a non-condensed polycyclic hydrocarbon compound.

10. The electrophotographic photoconductor as claimed in claim 9, wherein said non-condensed polycyclic hydrocarbon compound is selected from the group consisting of biphenyl, polyphenyl, diphenylalkane, diphenylpolyene, diphenylpoly-yne, triphenylmethane, distyrylbenzene, 1,1-diphenylcycloalkane, polyphenylalkane, and polyphenylalkene.

11. The electrophotographic photoconductor as claimed in claim 1, wherein by

is a bivalent group of a condensed polycyclic hydrocarbon compound.

12. The electrophotographic photoconductor as claimed in claim 11, wherein said condensed polycyclic hydrocarbon compound is selected from the group consisting of pentalenediyl, indenediyl, naphthalenediyl, azulenediyl, heptalenediyl, biphenylenediyl, as-indacenediyl, fluorenediyl, s-indacenediyl, acenaphthylenediyl, pleiadenediyl, acenaphthenediyl, phenalenediyl, phenanthrenediyl, anthracenediyl, fluoranthenediyl, ace-phenanthrylenediy, aceanthrylenediyl, triphenylenediyl, pyrenediyl, chrysenediyl, and naphthacenediyl.

13. The electrophotographic photoconductor as claimed in claim 1, wherein

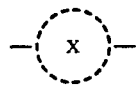

is a bivalent group of a hydrocarbon ring assembly.

14. The electrophotographic photoconductor as claimed in claim 13, wherein sad hydrocarbon ring assembly is 9,9-diphenylfluorene.

15. The electrophotographic photoconductor as claimed in claim 1, wherein

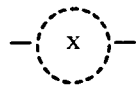

has a substituent selected from the group consisting of a halogen atom, a cyano group, a nitro group, an alkyl group having 1 to 12 carbon atoms, an alkoxyl group —OR$^5$, in which R$^5$ is an alkyl group having 1 to 12 carbon atoms, an aryloxy group with an aryl group selected from the group consisting of phenyl group and naphthyl group, a substituted mercapto group —SR$^6$, in which R$^6$ is an alkyl group having 1 to 12 carbon atoms or an aryl group selected from the group consisting of a non-condensed hydrocarbon group and a condensed polycyclic hydrocarbon group, a group

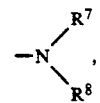

in which R$^7$ and R$^8$ each is hydrogen, an alkyl group having 1 to 12 carbon atoms, or an aryl group selected from the group consisting of phenyl group, biphenyl group, and naphthyl group, an alkylenedioxy group, and an alkylenedithio group.

16. The electrophotographic photoconductor as claimed in claim 1, wherein

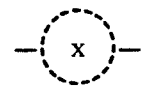

is selected from the group consisting of bivalent groups of carbazole, dibenzofuran, dibenzothiophene, oxadiazole, and thiadiazole.

17. The electrophotographic photoconductor as claimed in claim 1, wherein

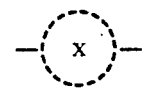

has a substituent selected from the group consisting of a halogen atom, a cyano group, a nitro group, an alkyl group having 1 to 12 carbon atoms, an alkoxyl group —OR$^5$, in which R$^5$ is an alkyl group having 1 to 12 carbon atoms, an aryloxy group with an aryl group selected from the group consisting of phenyl group and naphthyl group, a substituted mercapto group —SR$^6$, in which R$^6$ is an alkyl group having 1 to 12 carbon atoms or an aryl group selected from the group consisting of a non-condensed hydrocarbon group and a condensed polycyclic hydrocarbon group, a group

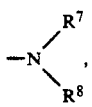

in which R$^7$ and R$^8$ each is an hydrogen, an alkyl group having 1 to 12 carbon atoms, or an aryl group selected from the group consisting of phenyl group, biphenyl group, and naphthyl group, an alkylenedioxy group, and an alkylenedithio group.

18. The electrophotographic photoconductor as claimed in claim 1, wherein said diamine compound is in an amount ranging from 30 wt. % to 70 wt. % of the entire weight of said photoconductive layer.

19. The electrophotographic photoconductor as claimed in claim 1, wherein said photoconductive layer has a thickness of 3 μm to 50 μm.

20. The electrophotographic photoconductor as claimed in claim 1, wherein said photoconductive layer comprises said charge generating material dispersed in a charge transporting medium which comprises said charge transporting material 21. The electrophotographic photoconductor as claimed in claim 1, wherein the amount of said diamine compound is in the range of 10 wt. % to 95 wt. % of the entire weight of said photoconductive layer, and the amount of said charge generating material is in the range of 0.1 wt. % to 50 wt. % of the entire weight of said photoconductive layer.

22. The electrophotographic photoconductor as claimed in claim 1, wherein said photoconductive layer comprises a charge generation layer comprising said charge generating material, and a charge transport layer comprising said charge transporting material.

23. The electrophotographic photoconductor as claimed in claim 22, wherein the amount of said charge generating material is in the range of 10 wt. % to 95 wt. % of the entire weight of said charge generation layer, and the amount of said diamine compound is in the amount of 10 wt. % to 95 wt. % of the entire weight of said charge transport layer.

* * * * *

UNITED STATES PATENT AND TRADEMARK OFFICE
CERTIFICATE OF CORRECTION

PATENT NO. : 5,312,707
DATED : May 17, 1994
INVENTOR(S) : MASAFUMI OTA ET AL

It is certified that error appears in the above-identified patent and that said Letters Patent is hereby corrected as shown below:

Column 2, line 36, delete "a" and insert --as--.

Column 28, line 6, insert after "skeleton" --(Japanese Laid-Open Patent Application 53-95033), an azo--.

Column 30, line 64, delete "(1-pyrenyl -N,N'" and insert therefor --(1-pyrenyl)-N,N'--

Column 33, line 1, delete "synthetic" and insert --synthesis--.

Column 38, Example 14, delete "(3.56" and insert --(3.56)--.

Column 53, line 46, before "Polyester", insert --"--.

Column 58, line 60, delete "an", first occurrence.

Signed and Sealed this

Second Day of May, 1995

*Attest:*

BRUCE LEHMAN

*Attesting Officer*  Commissioner of Patents and Trademarks